| United States Patent [19] | [11] | 4,371,617 |
|---|---|---|
| Tanaka et al. | [45] | Feb. 1, 1983 |

[54] PROCESS FOR PREPARING THIENAMYCIN

[75] Inventors: Kentaro Tanaka, Suita; Naoki Tsuji, Ashiya; Eiji Kondo, Ikeda; Yoshimi Kawamura, Minō, all of Japan

[73] Assignee: Shionogi & Co., Ltd., Osaka, Japan

[21] Appl. No.: 244,857

[22] Filed: Mar. 18, 1981

[30] Foreign Application Priority Data

Apr. 17, 1980 [JP] Japan ................... 55/51007

[51] Int. Cl.$^3$ ................ C12P 17/18; C12R 1/465
[52] U.S. Cl. ................... 435/119; 435/886
[58] Field of Search ......................... 435/119

[56] References Cited

U.S. PATENT DOCUMENTS

| 4,006,060 | 2/1977 | Kahan et al. | 435/119 |
| 4,247,640 | 1/1981 | Kempf et al. | 435/119 |
| 4,264,736 | 4/1981 | Cassidy et al. | 435/119 |

*Primary Examiner*—Alvin E. Tanenholtz
*Attorney, Agent, or Firm*—Wenderoth, Lind & Ponack

[57] ABSTRACT

A new process for preparing thienamycin, a known antibiotic useful as a medicament and veterinary drug, characterized by cultivating *Streptomyces penemifaciens* sp. nov. in a suitable medium and recovering thienamycin from the fermentation broth.

4 Claims, No Drawings

PROCESS FOR PREPARING THIENAMYCIN

This invention relates to a new process for preparing thienamycin with a strain of *Streptomyces penemifaciens* sp. nov. and mutants thereof.

The microbe to be used in this invention is a strain belonging to Actinomycetales. Taxonomical studies concluded that the microbe was a strain belonging to a new species of Streptomyces which was designated *Streptomyces penemifaciens* sp. nov. The type strain has been deposited in Fermentation Research Institute, Agency of Industrial Science & Technology, Yatabe-machi, Tsukuba-gun, Ibaragi Pref., Japan uder the accession number FERM-P No. 5305 since Dec. 10, 1979 and also in the American Type Culture Collection, Maryland, U.S.A. as ATCC No. 31599 since Feb. 7, 1980.

The inventors discovered that the microbe produced an antibiotic in the culture broth, which was isolated and identified with a known antibiotic thienamycin. Thienamycin is an antibiotic of the following structural formula and has been described in J. Antibiotics 32, 1 (1979), Antimicrobial Agents & Chemotherapy 15, 518 (1978) and Chemical Industry 1979 (October) 990.

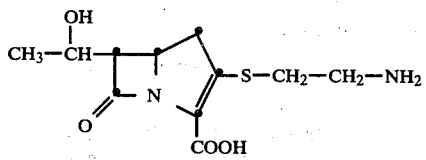

Thienamycin is a typical compound of penen-antibiotics and has a potent anti-microbial activity against both gram-positive and gram-negative bacteria. Furthermore, it is active against bacteria resisting $\beta$-lactam antibiotics such as penicillins and cephalosporins.

As for thienamycin-producing organisms, only one strain of bacteria, *Streptomyces cattleya* NRRL 8057 is known (Japanese patent Unexamined Publication No. 73191/1976). The production of thienamycin with this strain, however, is not satisfactory since the organism produces some undesired by-products such as penicillin N, cephamycin C, and the like which make the isolation procedure complicated. On the contrary, the organism isolated in the present invention produces no such by-products and thienamycin can readily be isolated from the culture broth.

The strain *Streptomyces penemifaciens* used in this invention has the following mycological properties:

(I) Morphological properties (Cultivation: Bennett's agar, 28° C., 14 days)

No sporangium, flagellated spore and sclerotium are observed. No fragmentation of vegetative mycelium occurs. Growth on this medium is good through formation of aerial mycelia and bearing of conidia are not good. Conidia-bearing hyphae are formed on aerial hyphae and simply branch from the main stem to form twigs, the end of which is spiral. A chain of conidia is not so long, consisting of less than 30. The surface of conidia is smooth as observed under an electron microscope.

(II) Cultural properties on various media (Cultivation: 28° C., 14 days)

The results are shown in Table I. The expression of color depends on "Guide to Color Standard" (published by Japan Color Institute).

Color of the aerial mycelium is white or light brownish gray on most media, namely the color is light brownish gray when formation of conidia is good.

TABLE I

| Medium | Growth | Aerial Mycelium Formation | Color | Color of Vegetative mycelium | Soluble Pigment |
|---|---|---|---|---|---|
| Sucrose nitrate agar | Good | Slight | White | Pale yellowish brown | None |
| Glucose asparagine agar | " | Good | " | Pale yellow to Pale yellowish brown | " |
| Glycerol asparagine agar | " | " | Light brownish gray | Pale yellowish brown | " |
| Inorganic salts starch agar | Moderate | Moderate | White to light brownish gray | " | " |
| Tyrosine agar | Good | Good | White to light brownish gray | " | " |
| Nutrient agar | Poor | None | — | " | " |
| Yeast extract malt extract agar | Moderate | Moderate | Light brownish gray to white | Yellowish brown | " |
| Oatmeal agar | " | Slight | Light brownish gray to white | Pale yellowish brown | " |
| Bennett's agar | Good | Moderate | Light brownish gray to white | " | " |

(III) Growth temperature (Cultivation on Bennett's agar medium for 2 weeks at each temperature as shown below except at 10° C. at which it was continued for 3 weeks)

10° C. No growth
28° C. Good growth, moderate formation of aerial mycelium
37° C. Good growth, moderate formation of aerial mycelium in the same degree as at 28° C.
higher than 45° C. No growth (IV) Physiological properties (Cultivation at 28° C. for 14 days)

| | |
|---|---|
| Production of melanoid pigment | Negative |
| Tyrosinase reaction | Negative |
| Coagulation of milk | Negative |
| Peptonization of milk | Negative |
| Liquefaction of gelatin | Negative |
| Hydrolysis of starch | Positive |

(V) Utilization of carbon source

L-arabinose, D-xylose, D-glucose, D-fructose, sucrose, innositol, L-rhamnose, raffinose, and D-mannitol are well utilized.

It is obvious from the above properties that the microbe belongs to Streptomyces. A search was made for a strain having the above properties in Wacksman's "The Actinomycetes" vol. 2 (1961), Shirling and Gottlieb's "Reports of International Streptomyces Project, International Journal of Systematic Bacteriology" vol. 18, 69 and 279 (1968), 19, 391 (1969) and 22, 265 (1972), "Bergey's Manual of Determinative Bacteriology" 8th ed. (1974) and other literatures describing new species of Streptomyces. As a result, *Streptomyces nigellus* disclosed in "International Journal of Systematic Bacteriology" vol. 22, 325 (1972) and U.S. Pat. No. 3,094,461 (1963) is recognized as the closest species because it has the common properties as follows:

(1) The color of the aerial mycellium belongs to the gray series.

(2) The chain of the conidia is spiral.

(3) The surface of the conidia is smooth.

(4) Production of melanoid pigment is negative. and (5) Various kinds of sugars are utilizable.

Accordingly, the strain PA-40702 and the type strain of *Streptomyces nigellus* (abbreviated *S. nigellus* hereinafter) were compared with each other directly and the differences were observed as follows:

(1) The strain PA-40702 is positive in hydrolysis of starch but *S. nigellus* is negative.

(2) The strain PA-40702 is negative in liquefaction of gelatin but *S. nigellus* is positive.

(3) No growth of the strain PA-40702 is observed at 10° C. although *S. nigellus* grows well.

(4) The strain PA-40702 produces thienamycin but the production by *S. nigellus* has not been reported nor been observed.

Also, the strain PA-40702 was compared with *Streptomyces cattleya* reported as a thienamycin-producing strain in Japanese Patent Unexamined Publication No. 73191/1976 and the differences were recognized as follows:

(1) The color of aerial mycelium of the strain PA-40702 belongs to the gray series but that of *S. cettleya* characteristically belongs to the violet series.

(2) The strain PA-40702 is negative in peptonization of milk and liquefaction of gelatin but *S. cattleya* is positive.

(3) The strain PA-40702 utilizes arabinose, innositol, raffinose and ramnose but *S. cattleya* does not use these carbon sources.

Accordingly, the strain PA-40702 obviously belongs to a different species from *S. cattleya*. Conclusively, the strain PA-40702 is determined to be a new species belonging to Streptomyces and designated as *Streptomyces penemifaciens* sp. nov.

The present invention includes all strains belonging to the above new species as well as the natural and artificial mutants. Namely, this invention includes any strain as long as it produces thienamycin and cannot be clearly distinguished from the species *Streptomyces penemifaciens*.

The process for preparing thienamycin of this invention is shown below. A thienamycin-producing strain of *Streptomyces penemifaciens* sp. nov. is cultivated in a medium containing various nutrients under aerobic conditions. The conditions for cultivation and the composition of medium are arranged according to the usual ones used for producing antibiotics. Namely, the medium basically contains carbon sources, nitrogen sources and inorganic salts. Vitamins, precursors and the like may be added, if necessary. There are exemplified glucose, sucrose, starch, dextrin, glycerol, molasses, organic acids and the like as carbon source, which are used singly or as a mixture. Nitrogen sources are, for example, soybean meal, corn steep liquor, meat extract, yeast extract, cotton seed meal, peptone, wheat germ, ammonium sulfate, ammonium nitrate and the like. They are used singly or as a mixture. Inorganic salts are, for example, calcium carbonate, sodium chloride, potassium chloride, magnesium sulfate, cobalt chloride, various phosphate and the like. They may be added to the medium, if necessary. Fermentation can be carried out in the same manner as used for production of usual antibiotics. Liquid fermentation is preferable and it is carried out preferably under submerged aerobic conditions. The pH of the medium is about 5.5 to 8.5. The temperature for fermentation is about 20° to 40° C. Anti-foaming agents may be added, if necessary, before or during the fermentation.

The isolation of thienamycin from the culture broth is carried out according to the usual manner when cultivation is completed. Filtration, absorption and desorption on various ion exchange resins, chromatography with various active adsorbents, extraction with various organic solents and the like are properly combined to obtain the objective thienamycin. Further, the objective compound can be isolated in the form of addition salts such as metal salts, e.g. sodium salt, acid salts, e.g. hydrochloride, sulfate, oxalte, succinate, and the like.

The thienamycin isolated and purified in the above manner has the physical properties as follows:

(1) UV absorption spectrum: $\lambda_{max}^{H2O\ (pH\ 4-8)}$ nm ($E_1\ cm^{1\%}$) 296.5 (290)

(2) IR absorption spectrum:
$\nu_{max}^{Nujol}$ 1765, 1650–1550 cm$^{-1}$ (3) CD spectrum:
287.0 nm (positive maximum),
216.0 nm (negative minimum)
(in potassium phosphate buffer, pH 7)

The thienamycin produced by this invention was identified with that produced by *Streptomyces cattleya* in comparison of physical constants and chromatographic behaviour.

A procedure for preparing the objective thienamycin is exemplified below but it can not be construed as limiting of this invention.

EXAMPLE (a) Fermentation

Medium S (seed medium): 0.5% soluble starch, 0.5% glucose, 0.5% polypeptone, 0.5% meat extract, 0.25% yeast extract, 0.25% sodium chloride, and deionized water (pH 7, before sterilization)

Medium B (fermentation medium): 2.0% corn meal, 1.5% soybean meal, 0.4% sodium citrate, 0.05% potassium chloride, 0.01% magnesium sulfate, and water (pH 6.5, before sterilization)

Seed culture slant of *Streptomyces penimifaciens* PA-40702 (FERM-P No. 5305, ATCC No. 31599) is inoculated into 800 ml Medium S of the above composition in a 2 L-Erlenmeyer flask and kept at 28° C. for 48 hours under shaking at 180 r.p.m. Each 800 ml of this culture broth is inoculated into 20 L Medium B of the above composition in a 30 L-jar and cultivated at 28° C. for 65 hours under aeration at 20 L/minute and stirring at 150–300 r.p.m. at an inner pressure of 0.2 kg/cm$^2$.

(b) Isolation

The culture broth obtained above is centrifuged by sharples centrifugation. The supernatant is separated, cooled at 5° C. and applied to column chromatography on Dowex 50×4 (Na+) (Dow Chemical Co., Ltd., U.S.A.). The column is eluted with 0.2% 2,4-lutidine. The eluate is passed through a column of Diaion HP-20 (Mitsubishi Chemical Industry) to remove the lutidine. Each fraction of the eluate is adjusted to pH 7.0 and the activity is checked by pulp disk diffusion method with *E. coli*. The active fractions are collected and lyophilized to give a crude powder of thienamycin. The product is passed through a column of Dowex AG 1×4 (Cl−), which is eluted with cold deionized water. The active fractions are collected and lyophilized. The product is further purified by high performance liquid chromatography using Nucleocil 5-$C_{18}$ (M. Nargel Co., Ltd., West Germany) to give thienamycin of the purity 90% or more. The product has the physical constants noted above and is identical with an authentic sample of thienamycin in comparison of various patterns on chromatography.

What we claim is:

1. A process for preparing thienamycin which comprises cultivating a thienamycin-producing strain of *Streptomyces penemifaciens* sp. nov. or a mutant thereof in a medium under aerobic conditions, and isolating the accumulated thienamycin from the cultured broth.

2. The process claimed in claim 1 wherein the thienamycin-producing strain is *Streptomyces penemifaciens* PA-40702, ATCC No. 31599.

3. The process claimed in claim 1 wherein the cultivation is effected at a pH from about 5.5 to 8.5 and at a temperature from about 20° to 40° C.

4. A biologically pure culture of *Streptomyces penimifaciens*, having the identifying characteristics of ATCC 31599, said culture being capable of producing thienamycin upon cultivation under aerobic conditions in a medium containing sources of carbon, nitrogen and inorganic salts.

* * * * *